United States Patent [19]

Werner

[11] 4,362,537
[45] Dec. 7, 1982

[54] METHOD FOR THE REMOVAL OF POLYMER FROM A PURGE MEDIUM IN A MONOOLEFIN ADSORPTION - DESORPTION SEPARATION PROCESS

[75] Inventor: Robert G. Werner, Danbury, Conn.

[73] Assignee: Union Carbide Corporation, Danbury, Conn.

[21] Appl. No.: 238,843

[22] Filed: Feb. 27, 1981

[51] Int. Cl.³ .............................................. B01D 53/04
[52] U.S. Cl. ............................................. 55/62; 55/75; 585/826
[58] Field of Search ................. 55/62, 75; 203/41, 71; 208/310 Z; 585/821, 826, 828

[56] References Cited

U.S. PATENT DOCUMENTS

| | | | |
|---|---|---|---|
| 3,146,277 | 8/1964 | Hawes et al. | 55/75 X |
| 3,184,518 | 5/1965 | Sanders et al. | 55/75 X |
| 3,201,490 | 8/1965 | Lacey et al. | 55/75 |
| 3,226,914 | 1/1966 | Griesmer et al. | 55/75 X |
| 3,422,003 | 1/1969 | Anstey et al. | 585/826 X |
| 3,422,005 | 1/1969 | Avery | 585/826 X |
| 3,539,502 | 11/1970 | Griswold | 585/826 X |
| 3,619,409 | 11/1971 | Stokeld, Jr. | 585/826 X |
| 3,619,418 | 11/1971 | Lewis | 585/826 X |
| 3,717,572 | 2/1973 | de Gramont et al. | 55/75 X |
| 3,721,064 | 3/1973 | Symoniak et al. | 55/62 |
| 3,753,896 | 8/1973 | Bryan et al. | 585/826 X |

*Primary Examiner*—Robert H. Spitzer
*Attorney, Agent, or Firm*—Harrie M. Humphreys

[57] ABSTRACT

A method for the removal of polymer from a straight-chain paraffin purge medium used in a monoolefin adsorption-desorption separation process comprising recycling a countercurrent purge step polymer containing straight-chain paraffin product for use as purge medium in the process without separation of polymer from the straight-chain paraffin and separating polymer from at least a portion of an adsorption step and a copurge step polymer containing straight-chain paraffin product and recycling the purified straight-chain paraffin for use as purge medium in the process.

7 Claims, 3 Drawing Figures

METHOD FOR THE REMOVAL OF POLYMER FROM A PURGE MEDIUM IN A MONOOLEFIN ADSORPTION - DESORPTION SEPARATION PROCESS

This invention relates to a method for the removal of polymer from a purge medium in an adsorption-desorption process for the separation of straight-chain monoolefin from branched-chain monoolefin.

BACKGROUND OF THE INVENTION

It is known that straight-chain monoolefin may be separated from branched-chain monoolefin by processes employing molecular sieve having a pore diameter of about 5 Angstroms. These processes are based on the well known acceptance-exclusion principle based on molecular size. A molecular sieve which has a pore diameter of about 5 Angstroms, will accept or adsorb straight-chain monoolefin. Such processes are described, for example, in U.S. Pat. No. 3,721,064 to Symoniak et al. and U.S. Pat. No. 3,717,572 to de Gramont et al.

Such processes may be used for the separation of straight-chain monoolefin from branched-chain monoolefin from feed mixtures of the four, five, and six carbon monoolefins. Such processes are particularly useful for the separation of mixed butene feeds into straight-chain butene monoolefin and branched-chain isobutylene monoolefin. Isobutylene is used, for example, in the manufacture of butyl rubber, polyisobutylenes and in the production of gasoline alkylate. Straight-chain normal butene monoolefins include butene-1, trans-butene-2, and cis-butene-2 which are used, for example, in the production of secondary butyl alcohol and methyl ethyl ketone. In some instances, the straight-chain butenes product is further separated, e.g., by fractional distillation, to obtain a butene-1 product which may be used, for example, as in the manufacture of polyethylene copolymers.

If a monoolefin feed contains butenes, pentenes and hexenes, it is considered advantageous to prefractionate the feed and operate the separation process on a monoolefin feed having a single carbon number.

A suitable molecular sieve for use in such a separation process as an adsorbent is synthetic zeolite type A in its calcium cation exchanged form known as type 5A or its high calcium cation form. Type 5A and high calcium exchanged type 5A molecular sieve may be obtained from Union Carbide Corporation, New York, N.Y. Other useful zeolites of natural origin or synthesized having pore sizes of about 5 Angstroms include chabazite, mordenite, gmelinite, erionite and those known as types D, R, S, and T.

In general, the separation process comprises an adsorption step wherein a hydrocarbon vapor feed stream containing straight-chain monoolefin and branched-chain monoolefin is passed into one end of an adsorber containing a molecular sieve having a pore diameter of about 5 Angstroms. The molecular sieve has adsorbed thereon straight-chain paraffinic hydrocarbon, most suitably normal hexane. A first effluent stream is obtained from the other end of the adsorber. The first effluent stream contains branched-chain monoolefin and the straight-chain paraffin hydrocarbon. Straight-chain monoolefin has been adsorbed by the molecular sieve.

A copurge or cocurrent purge step is then practiced. A straight-chain paraffinic hydrocarbon vapor stream, most suitably normal hexane, is passed into said one end of the adsorber and a second effluent stream comprising branched-chain monoolefin and straight-chain paraffin hydrocarbon is obtained from said other end of the adsorber. Straight-chain paraffin hydrocarbon is adsorbed by the molecular sieve. Most suitably, sufficient molecular sieve adsorbent has not been utilized in the adsorption step so that substantially all the straight-chain monoolefin will remain adsorbed in the adsorbent bed and will not break through and exit with the second effluent stream. The copurge step is suitably continued until substantially all of the branched-chain monoolefin has exited the adsorber in the second effluent stream.

Next, a desorption or countercurrent purge step is practiced. A straight-chain paraffinic hydrocarbon vapor stream, most suitably normal hexane, is passed into said other end of the adsorber. A third effluent stream comprising straight-chain monoolefin and straight-chain paraffinic hydrocarbon is obtained from said one end of the adsorber. The countercurrent purge step is suitably continued until substantially all of the straight-chain monoolefin has exited the absorber in the third effluent stream. The straight-chain paraffinic hydrocarbon is adsorbed on the molecular sieve during the countercurrent purge step.

The absorption step is again practiced and the process cycle repeated as desired.

The branched-chain monoolefin and straight-chain paraffinic hydrocarbon in the first and second effluent streams are separated, e.g., by fractional distillation, to obtain as overhead a purified branched-chain monoolefin product and as bottoms a straight-chain paraffinic hydrocarbon.

The straight-chain monoolefin and straight-chain paraffinic hydrocarbon in the third effluent stream are separated, e.g., by fractional distillation, to obtain as overhead a purified straight-chain monoolefin product and as bottoms a straight-chain paraffinic hydrocarbon.

It is very desirable, from an economic and process efficiency viewpoint, to recycle the separated straight-chain paraffinic hydrocarbons as purge for use in subsequent process cycles.

It is known that such a separation process results in the formation of polymers. Polymer which forms in the adsorber appears in the separated straight-chain paraffinic hydrocarbon which is going to be recycled for purge. As a result, there will be a continuous buildup of polymer in the recycled straight-chain paraffinic hydrocarbon purge medium unless polymer is removed. Such a polymer build up is disadvantageous because it can lead to adsorbent deactivation.

OBJECT OF THE INVENTION

It is therefore an object of the present invention to provide an improved method for the removal of polymer from a straight-chain paraffinic purge medium used in an adsorption-desorption process for the separation of straight-chain monoolefin from branched-chain monoolefin.

It is a further object of the present invention to provide an improved method for the removal of polymer from a straight-chain paraffinic purge medium used in an adsorption-desorption process for the separation of straight-chain monoolefin from branched-chain monoolefin which reduces the size and utilities requirements for a fractional distillation column used for the separation of polymer from a straight-chain paraffinic purge medium.

These and other objects will be apparent from the following description and claims in conjunction with the drawings.

SUMMARY OF THE INVENTION

The present invention may be generally summarized as:

A process for the separation of hydrocarbons in a vapor feed stream containing straight-chain and branched-chain monoolefin having from four to six carbon atoms inclusive comprising:

as an adsorption step,
  passing said vapor feed stream into one end of an adsorber containing molecular sieve having a pore diameter of about 5 Angstroms; and
  obtaining from the other end of said adsorber a first effluent fluid stream exiting in vapor phase comprising branched-chain monoolefin, branched-chain polyolefin, and straight-chain paraffin hydrocarbon;

as a copurge step,
  passing a first vapor purge stream containing straight-chain paraffin hydrocarbon into said one end of said adsorber; and
  obtaining from said other end of said adsorber a second effluent fluid stream exiting in vapor phase comprising branched-chain monoolefin, branched-chain polyolefin, and straight-chain paraffin hydrocarbon;

as a countercurrent purge step,
  passing a second vapor purge stream containing a straight-chain paraffin hydrocarbon into said other end of said adsorber; and
  obtaining from said one end of said adsorber a third effluent fluid stream exiting in vapor phase comprising straight-chain monoolefin, branched-chain polyolefin, and straight-chain paraffin hydrocarbon;

wherein the partial pressure of the straight-chain paraffin hydrocarbon content of said first and second vapor purge streams is greater than the partial pressure of the straight-chain monoolefin content of the vapor feed stream, and wherein said molecular sieve is partially loaded with straight-chain paraffin hydrocarbon during all of said adsorption, copurge and countercurrent purge steps; and separating said branched-chain monoolefin from said branched-chain polyolefin and said straight-chain paraffin hydrocarbon in said first and second effluent fluid streams, said separation providing a fourth effluent fluid stream comprising branched-chain polyolefin and straight-chain paraffin hydrocarbon;

separating said straight-chain monoolefin from said branched-chain polyolefin and said straight-chain paraffin hydrocarbon in said third effluent fluid stream, said separation providing a fifth effluent fluid stream comprising branched-chain polyolefin and straight-chain paraffin hydrocarbon;

the improvement in which comprises:
  (a) recycling said fifth effluent fluid stream comprising branched-chain polyolefin and straight-chain paraffin hydrocarbon for use in said first and second purge streams without separation of said branched-chain polyolefin from said straight-chain paraffin hydrocarbon in said fifth effluent fluid stream;
  (b) introducing at least a portion of said fourth effluent fluid stream into a separation unit for separating said branched-chain polyolefin from said straight-chain paraffin hydrocarbon and obtaining from said separation unit a sixth effluent fluid stream comprising straight-chain paraffin hydrocarbon and a seventh effluent fluid stream comprising branched-chain polyolefin; and
  (c) recycling said sixth effluent fluid stream comprising straight-chain paraffin hydrocarbon for use in said first and second purge streams.

DESCRIPTION OF THE PREFERRED EMBODIMENT

In order to afford a complete understanding of the present invention and an appreciation of its advantages, a description of the preferred embodiments is presented below.

Figure 1:
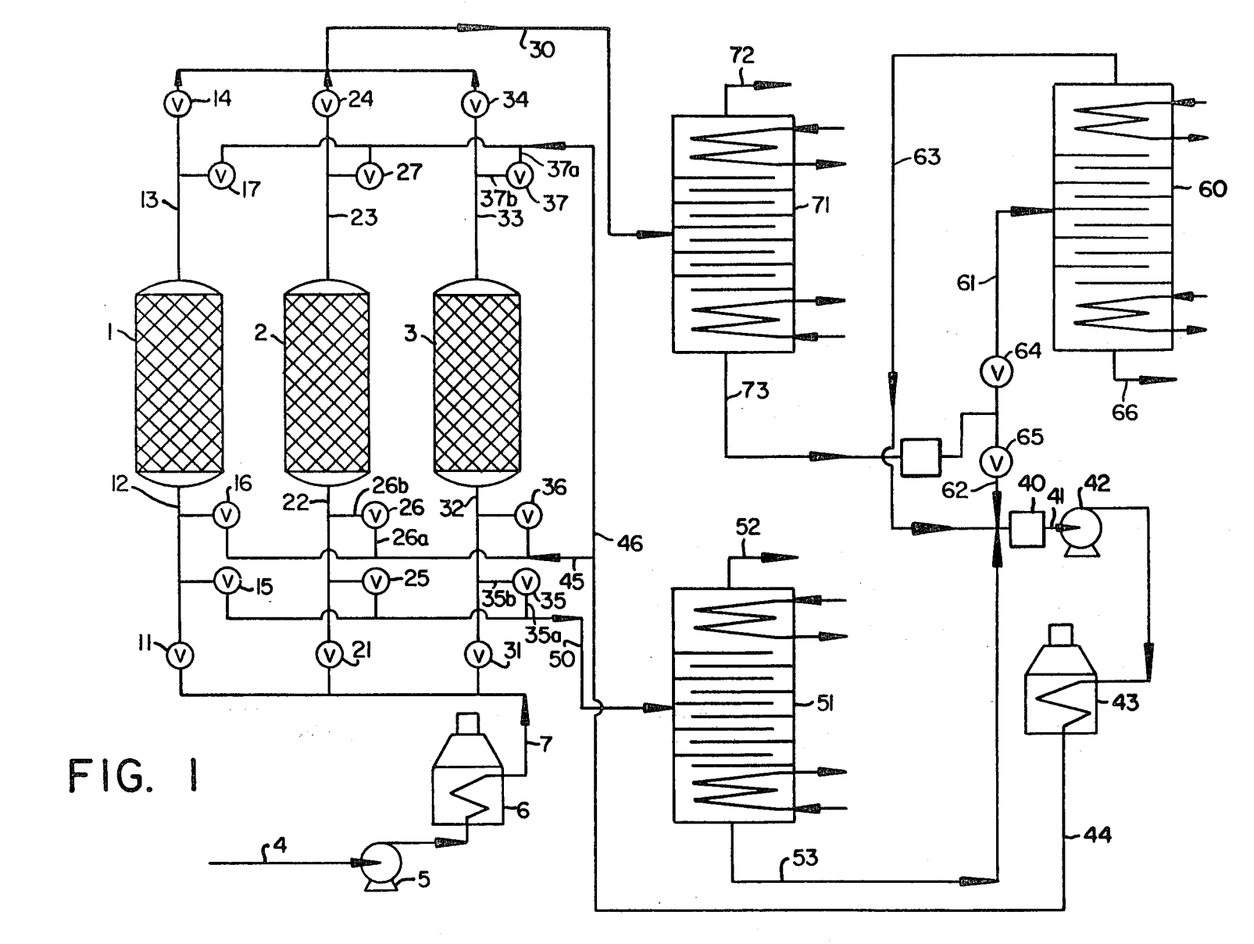
FIG. 1 is a schematic flow diagram illustrating a preferred arrangement for the practice of the method of the present invention with a three bed adsorber separation system.

Referring to FIG. 1, adsorber 1, adsorber 2, and adsorber 3 each contain molecular sieve having a pore diameter of about 5 Angstroms of the type hereinbefore described. The molecular sieve is preferably in the form of extruded or beaded particles, e.g., 1/16 inch pellets.

Adsorber 1 is placed on its adsorption step having been previously on its countercurrent purge step or desorption step. Adsorber 2 is placed on its copurge step having been previously on its adsorption step. Adsorber 3 is placed on its countercurrent purge step or desorption step having been previously on its copurge step.

Adsorber 1, adsorber 2, and adsorber 3 are each at process temperature and pressure. Process temperature is suitably about 150° F. to 250° F. and most suitably about 210° F. to 230° F. Process pressure is suitably about 0 psig to 100 psig and most suitably about 0 psig to 20 psig.

Adsorber 1, placed on its adsorption step, contains normal hexane vapor therein and the molecular sieve adsorbent bed of adsorber 1 contains adsorbed normal hexane equivalent to process temperature and pressure conditions. A hydrocarbon feed stock containing normal butenes as straight-chain monoolefin and isobutylene as branched-chain monoolefin enters conduit 4 and is pumped to process pressure (e.g., about 10 psig) in pump 5 (if required) and heated to process temperature (e.g., about 100° C.) in heater 6 and passes through conduit 7, inlet valve 11 and conduit 12 into adsorber 1 containing the molecular sieve adsorbent. Similarly, feedstock is admitted to adsorber 2 via inlet valve 21, and adsorber 3 via inlet valve 31, when the adsorbers are in their respective adsorption steps. The hydrocarbon feed stream vapor passes upwardly through the molecular sieve bed contained in adsorber 1 displacing the normal hexane in the vapor phase and in the adsorbed phase toward the top and out through conduit 13. As the normal hexane partial pressure in the gas phase is reduced, desorption of normal hexane from the molecular sieve adsorbent occurs and normal olefin, including straight-chain butene-1, is adsorbed while branched-chain olefin, including isobutylene, remains in the gas or vapor phase and flows out conduit 13 in mixture with normal hexane vapor as an effluent from adsorber 1.

The normal hexane desorption and the straight-chain olefin adsorption action proceeds upwardly through the bed but is not evidenced by a notable temperature gradient. It is to be recognized that the desorption of the normal hexane is endothermic and the adsorption of the straight-chain olefin is exothermic and that the net effect of this desorption-adsorption action is exothermic but the net heat release by the desorption-adsorption action is small.

The normal hexane desorption and the straight-chain olefin adsorption action occurs in a particular portion of the molecular sieve bed as the partial pressure of the normal hexane gas phase decreases and the partial pressure of the straight-chain olefin gas phase increases in that portion of the bed. Such desorption-adsorption action is well known in the art.

The adsorption step may be terminated upon or shortly after the appearance of straight-chain olefin in an increasing concentration in the effluent, but it is advantageously terminated earlier since any straight-chain olefin exiting during the adsorption step will be found as an impurity in the purified branched-chain olefin product. Furthermore, any straight-chain olefin exiting with the effluent will not be recovered as purified normal olefin product. The most advantageous point for termination of the adsorption step is earlier than when there will be an increasing appearance or breakthrough of normal olefin in the effluent during the latter part of the copurge step for the adsorber which will follow.

During the adsorption step, the effluent vapor stream passing from absorber 1 through conduit 13, is passed through valve 14 and conduit 30 to fractional distillation column 71 from which branched-chain olefin purified product (i.e., isobutylene product) is taken as overhead through conduit 72 and normal hexane is taken as bottoms from conduit 73. Although the adsorption step effluent fluid stream exits adsorber 1 in vapor phase, it may enter fractional distillation column 71 in either liquid or vapor phase depending upon the design of the particular system employed.

The composition of the adsorption step effluent changes as the adsorption step progresses from a high concentration of normal hexane to a lower concentration while the concentration of branched-chain olefin increases.

Adsorber 2, placed on its copurge step having completed its adsorption step, contains straight-chain olefin and branched-chain olefin and normal hexane in the gas or vapor phase. It is the purpose of the copurge step to transfer at least a major amount of the branched-chain olefin left in the adsorber after the adsorption step to the branched-chain olefin distillation and product recovery system.

The molecular sieve having a pore diameter of about 5 Angstroms contained in adsorber 2 will have adsorbed between straight-chain olefin and normal hexane.

In the copurge step, normal hexane from reservoir 40 enters conduit 41 and is pumped to process pressure (e.g., about 10 psig) in pump 42, heated to process temperature (e.g., about 100° C.) in heater 43, and passed through conduit 44, conduit 45, conduit 26a, valve 26, conduit 26b, and conduit 22 into adsorber 2. Similarly, normal hexane is admitted to adsorber 1 via valve 16, and adsorber 3 via valve 36, when the adsorbers are in their respective copurge steps. Adsorber 2 is in a flow through state so that as the vapor purge stream containing the normal hexane gas enters via conduit 22, an effluent vapor stream exits adsorber 2 via conduit 23.

As the normal hexane purge gas moves upwardly through the molecular sieve bed of adsorber 2, the partial pressure of normal hexane gas is increasing and will thus effect desorption of straight-chain olefin from and adsorption of the normal hexane by the molecular sieve in a manner well known in the art. The desorbed straight-chain olefins move upwardly in the bed and will be subsequently adsorbed in the portion of the molecular sieve bed that was not utilized for straight-chain olefin adsorption in the preceding adsorption step for adsorber 2.

The effluent vapor stream contains branched-chain olefin and normal hexane and straight-chain olefin to the extent that straight-chain olefin is not adsorbed by upper portions of the molecular sieve bed which were not utilized for straight-chain olefin adsorption in the preceding adsorption step for adsorber 2.

As the copurge step continues, the branched-chain olefin concentration of the effluent vapor stream will decrease. The copurge step will most advantageously continue until substantially all the branched-chain olefin has exited the molecular sieve bed in the effluent vapor stream, for reasons hereinafter discussed.

In the most advantageous practice of the present invention, a sufficient amount of the molecular sieve bed will not have been utilized as straight-chain olefin adsorbent in the adsorption step so that only minor amounts of straight-chain olefin will exit the adsorber in the copurge effluent vapor stream in a subsequent copurge step. That is, there will be only minor amounts of straight-chain olefin in the copurge effluent vapor stream to be available as an impurity in the purified branched-chain olefin product.

The partial pressure of the normal hexane content of the copurge vapor stream entering the adsorber in the copurge step will be greater than the partial pressure of the straight-chain olefin content of the vapor feed stream in the preceding adsorption step.

The copurge effluent vapor stream exits adsorber 2 through conduit 23, valve 24, and conduit 30 to fractional distillation column 71 where its olefin components become part of the overhead product (i.e., isobutylene rich) exiting through conduit 72 and its normal hexane component becomes part of the bottoms product exiting through conduit 73. Although the copurge step effluent fluid stream exits adsorber 2 in vapor phase, it may enter fractional distillation column 71 in either liquid or vapor phase depending upon the design of the particular system employed.

The copurge step may be referred to as a cocurrent purge since the purge vapor stream is entering the same end of the adsorber as the vapor feed stream in the preceding adsorption step.

Adsorber 3, placed on its countercurrent purge step, having completed its copurge step, contains normal hexane and some straight-chain olefin in the gas or vapor phase. In the most advantageous practice of the present invention, only minor amounts of branched-chain olefins will be present.

The molecular sieve having a pore diameter of about 5 Angstroms contained in adsorber 3 will have adsorbed thereon straight-chain olefin and normal hexane.

The purpose of the countercurrent purge step is to transfer at least a major portion of the straight-chain olefins to a straight-chain olefin distillation and product recovery system.

In the countercurrent purge step, normal hexane from reservoir 40 enters conduit 41 and is pumped to process pressure (e.g., about 10 psig) in pump 42, heated to process temperature (e.g., about 100° C.) in heater 43 and passes through conduit 44, conduit 46, conduit 37a, valve 37, conduit 37b, and conduit 33 into absorber 3. Similarly, normal hexane is admitted to absorber 1 via valve 17, and absorber 2 via valve 27, when the absorbers are in their respective countercurrent purge steps. Absorber 3 is in a flow through state so that as the countercurrent vapor purge stream enters via conduit 33, an effluent vapor stream exits absorber 3 via conduit 32.

As the normal hexane gas moves downwardly through the molecular sieve bed of absorber 3, desorption of straight-chain olefin and absorption of the normal hexane by the molecular sieve will be effected. This absorption-desorption action occurs without a noticable temperature change. It is, however, to be recognized in this instance, the adsorption-desorption action has a net endothermic effect but the net heat adsorbed is small.

The partial pressure of the normal hexane content of the countercurrent purge vapor stream entering the adsorber in the countercurrent purge step will be greater than the partial pressure of the straight-chain olefin content of the vapor feed stream in the preceding adsorption step. Accordingly, continuing the countercurrent purge step for a sufficient time will insure that substantially all straight-chain olefin is desorbed and removed from the bed exiting via the countercurrent purge effluent vapor stream.

The countercurrent purge effluent vapor stream will contain straight-chain olefin and normal hexane. In the most advantageous practice of the invention, there will be only minor amounts of branched-chain olefins in the countercurrent purge effluent vapor stream since substantially all the branched-chain olefins were removed from the adsorber in the preceding adsorption and copurge steps. Accordingly, only minor amounts of branched-chain olefin impurities will be present in the recovered straight-chain olefin product.

The countercurrent purge step is advantageously continued until substantially all straight-chain olefins are removed from the molecular sieve bed. At the conclusion of the countercurrent purge step, the adsorber contains gas or vapor phase normal hexane and the molecular sieve bed of the adsorber contains adsorbed normal hexane equivalent to process temperature and pressure conditions.

During the countercurrent purge, the effluent vapor stream exits the bottom of adsorber 3 via conduit 32, conduit 35b, valve 35, conduit 35a and conduit 50 to fractional distillation column 51. Purified straight-chain olefin product (including butene-1) is recovered as overhead exiting through conduit 52 and normal hexane is recovered as bottoms product exiting fractional distillation column 51 through conduit 53. Although the countercurrent purge step effluent fluid stream exits adsorber 3 in vapor phase, it may enter fractional distillation column 51 in either liquid or vapor phase depending upon the design of the particular system employed.

After adsorber 1 has completed its adsorption step, adsorber 2 has completed its copurge step, and adsorber 3 has completed its countercurrent purge step, the operation is repeated by placing adsorber 1 on its copurge step, adsorber 2 on its countercurrent purge step and adsorber 3 on its adsorption step. After this operation is completed, another operation is repeated by placing adsorber 1 on its countercurrent purge step, adsorber 2 on its adsorption step and adsorber 3 on its copurge step. It will be readily apparent to one skilled in the art that the process may be continuously repeated until the molecular sieve adsorbent becomes deactivated and is required to be regenerated. Methods for regenerating a deactivated molecular sieve adsorbent are well known in the art.

It will be apparent to one skilled in the art that the process may be advantageously practiced in a three bed system with the time for the adsorption step, the copurge step and the countercurrent purge step being substantially equal. The process may also be practiced with the time of the adsorption step, the copurge step, and the countercurrent purge step not being equal.

It will also be apparent to one skilled in the art that the process may be practiced with a two bed system such as described in U.S. Pat. No. 3,721,064 to Symoniak et.al. or that a one bed system wherein an individual adsorber alternately goes through an adsorption step, a copurge step and a countercurrent purge step may be readily employed. Moreover, it will be readily apparent to one skilled in the art that the process may be readily employed with a four or more adsorber bed system.

When an individual adsorber completes an adsorption step, a copurge step and a countercurrent purge step, it is referred to as having completed a cycle whether the individual adsorber is in a one bed, two bed, three bed etc. system.

It is known in the art that an adsorption-desorption type separation process as described in the foregoing results in the formation of polymer associated with the polymerization of olefin. Such polymers exit an adsorber with the adsorption step effluent, the copurge step effluent, and the countercurrent purge step effluent. Such polymers are formed in the adsorber and are substantially all branched-chain polyolefins.

That is, in an adsorption step, the effluent fluid stream exiting an adsorber in vapor phase comprises branched-chain monoolefin, normal hexane and branched-chain polyolefin. In a copurge step, the effluent fluid stream exiting an adsorber in vapor phase comprises branched-chain monoolefin, normal hexane, and branched-chain polyolefin. In a countercurrent purge step, the fluid stream exiting an adsorber in vapor phase comprises straight-chain monoolefin, normal hexane, and branched-chain polyolefin.

Referring to FIG. 1, the fluid stream, which may be either vapor or liquid phase, passing through conduit 30 and entering fractional distillation column 71 is composed of adsorption step and copurge step effluent fluid streams exiting adsorbers 1, 2, or 3, (when either on adsorption or copurge step), via conduits 13, 23, and 33 and valves 14, 24, and 34 respectively, and thus comprises branched-chain monoolefin, normal hexane and branched-chain polyolefin. The fluid stream, which may be either vapor or liquid phase, passing through conduit 50 and entering fractional distillation column 51 is composed of countercurrent purge step effluent fluid streams exiting adsorbers 1, 2, or 3, (when on countercurrent purge step), via conduits 12, 22, and 32 and valves 15, 25, and 35 respectively and thus comprises straight-chain monoolefin, normal hexane and branched-chain polyolefin.

It is apparent that it would be advantageous to recycle the normal hexane product recovered as bottoms from fractional distillation column 71 and fractional distillation column 51 as purge for subsequent copurge and countercurrent purge steps. However, this normal hexane contains branched-chain polyolefin which is formed in the adsorbers during the separation process. Recycling of normal hexane purge medium containing polyolefin could lead to a polymer build up resulting in possible fouling of the molecular sieve adsorbent bed in the adsorbers. The prior art approach to alleviate this problem, described for example in U.S. Pat. No. 3,721,064 to Symoniak et. al., is to pass the hexane purge medium containing the polyolefin through a separation unit, such as a fractional distillation column, to obtain a clean hexane product as overhead for recycle as a purge medium. For economic reasons, the prior art typically did not distill or separate 100 percent of the polymer containing normal hexane purge medium. Typically about 20 to 30 percent of the recycled polymer containing normal hexane purge medium was redistilled. Thus some polyolefins were always present in the recycled normal hexane purge medium but not at levels to significantly impair process efficiency.

The present invention is predicated upon the discoveries that (1) very little of the polyolefin formed in an adsorber exits the adsorber with the countercurrent purge step effluent fluid stream relative to the amount of polyolefin formed in an adsorber that exits the adsorber with the adsorption step and copurge step effluent fluid streams and (2) the amount of polyolefin exiting an adsorber in the countercurrent purge step effluent stream is nearly the same as the amount of polyolefin in the normal hexane purge medium used as purge in the copurge and countercurrent purge steps.

Accordingly, in accordance with the process of the present invention, none of the polymer containing normal hexane product recovered as bottoms from fractional distillation column 51 (which separates the straight-chain monoolefin from the normal hexane and polyolefin in the countercurrent purge step effluent fluid stream) is subject to any separation process for the separation of polyolefin from the normal hexane prior to being recycled as purge in subsequent copurge and countercurrent purge step. Stated otherwise, in accordance with the process of the present invention, the branched-chain polyolefin containing normal hexane fluid effluent stream recovered from a normals product dehexanizer separation unit (e.g., fractional distillation column 51) is recycled for use as a purge medium for a copurge step and a countercurrent purge step without separation of branched-chain polyolefin polymer from the straight-chain normal hexane purge medium.

Referring to FIG. 1, a bottoms product fluid effluent stream comprising straight-chain normal hexane and relatively small amounts of branched-chain polyolefin exits normals product dehexanizer fractional distillation column 51 via conduit 53 and enters purge medium reservoir 40. The bottoms product effluent fluid stream exiting fractional distillation column 51 may be either in vapor or liquid form depending on the particular system design selected. The fluid in reservoir 40 is typically in liquid phase. The fluid in reservoir 40 is available for recycle as purge medium in copurge steps and countercurrent purge steps as hereinbefore described.

A bottoms product fluid effluent stream comprising straight-chain normal hexane and relatively large amounts of branched-chain polyolefin exits isomerproduct dehexanizer fractional distillation column 71 via conduit 73. At least a portion of fractional distillation column 71 bottoms product effluent fluid stream enters polymer removal fractional distillation column 60 via conduit 61. The remaining portion of the fractional distillation column 71 bottoms product effluent fluid stream enters purge medium reservoir 40 and is available for recycle as purge medium in copurge steps and countercurrent purge steps as hereinbefore described without having the branched-chain polyolefin separated from the straight-chain normal hexane purge medium.

The portion of the fractional distillation column 71 bottoms product fluid effluent stream entering polymer removal fractional distillation column 60 is separated into a normal hexane overhead product effluent fluid stream which exits fractional distillation column 60 via conduit 63 and enters purge medium reservoir 40 and is available for recycle as purge medium in copurge steps and countercurrent purge steps as hereinbefore described. Fractional distillation column 60 would typically provide a purified normal hexane overhead product from which about 90 percent or greater of the branched-chain polyolefin present in the portion of fractional distillation column 71 bottoms product effluent fluid stream that enters fractional distillation column 60 via conduit 61 has been removed.

A branched-chain polyolefin product is recovered as a bottoms product from polymer removal fractional distillation column 60 and exits as a fluid effluent stream via conduit 66. This polymer product may be used, for example, as alkylate or fuel.

The portion of the fractional distillation column 71 bottoms product effluent fluid stream entering polymer removal fractional distillation column 60 via conduit 61 and the portion routed directly to purge medium reservoir 40 may be selected by use, for example, of suitable flow control valves 64 and 65 or other suitable flow control devices.

Suitably at least about 25 percent and advantageously about 50 percent to 100 percent of fractional distillation column 71 bottoms product effluent fluid stream will be routed to polymer removal fractional distillation column 60 for separation of branched-chain polyolefin polymer from the normal hexane to be recycled as purge medium. If desired, the entire fractional distillation column 71 bottoms product fluid effluent stream may be routed via conduit 61 to polymer removal fractional distillation column 60 for removal of branched-chain polyolefin polymer from the normal hexane to be recycled as purge medium.

The fluid streams exiting fractional distillation column 71, entering fractional distillation column 60 and exiting fractional distillation column 60 may be either vapor or liquid phase depending on the particular system design selected.

The purge medium in the foregoing process has been described as normal hexane which has been found to be advantageously used in the process. However, the purge medium may be a straight-chain paraffinic hydrocarbon having one to three, advantageously two, more carbon atoms than the olefin hydrocarbon feed to be separated. The adsorption affinity of the molecular sieve for the adsorbing straight-chain olefin and the adsorbing straight-chain paraffin will thus be substantially equal so as to minimize the heat release of the exothermic adsorption-desportion action during the adsorption step so that there is no noticable, that is, so high heat zone developed.

As used in the description and claims, the separation (adsorption step, copurge step and countercurrent purge step) in an adsorber is said to be both isobaric and isothermal meaning that the hydrocarbon feed, copurge and countercurrent purge streams are both pressurized and heated to essentially the same degree.

Since the separation in an adsorber (adsorption step, copurge step and countercurrent purge step) is vapor phase, when selecting the upper pressure for a given temperature or the lower temperature for a given pressure, the limiting criteria is the dew point of the paraffin purge stream.

The separation in an adsorber (adsorption step, copurge step and countercurrent purge step) is advantageously practiced at lower rather than higher temperatures because higher temperatures tend to increase disadvantageous side reactions such as polymerization. However, the low temperature is determined by the condensation point or dew point of the paraffin purge at the selected adsorption-desorption process pressure.

It is believed that the branched-chain polyolefin polymer formed in an adsorber are primarily dimer addition type products of branched-chain olefins. This is stated by way of a possible explanation but is not intended to limit the scope of the present invention.

In order to more fully illustrate the present invention and to gain a further appreciation of its advantages the following example is set forth.

EXAMPLE

The hereinbefore described separation process comprising an adsorption step, a copurge step and a countercurrent purge step was practiced using a 14 foot conduit column having about a three inch diameter as a reactor to simulate a one bed adsorber system. The reactor conduit contained a molecular sieve zeolite (having a pore diameter of about 5 Angstroms) adsorbent bed.

The hydrocarbon vapor feed stream to be processed had a nominal composition as listed in Table I.

TABLE I

| FEED STREAM COMPOSITION | |
|---|---|
| COMPONENT | Wt. % |
| Propane | 0.69 |
| Isobutane | 2.78 |
| N—butane | 0.13 |
| Butene-1 | 35.33 |
| Isobutylene | 60.75 |
| Trans-butene-2 | 0.24 |
| Cis-butene-2 | 0.08 |

Process temperature was about 220° F. Process pressure was about 10 psig.

A cycle comprises an adsorption step, a copurge step and a countercurrent purge step. The cycle time for all runs of the example was about 24 minutes. The cycle time was distributed among the cycle steps as follows:

Adsorption step —8 minutes with a hydrocarbon vapor feed stream of Table I at a feed rate of about 178 cc/min. (liquid).

Copurge step—8 minutes with a technical grade normal hexane purge medium with a purge stream feed rate of about 138 cc/min (liquid).

Countercurrent purge step—8 minutes with a technical grade normal hexane purge medium with a purge stream feed rate of about 468 cc/min. (liquid).

The hydrocarbon feed and the purge feed were predried over zeolite since predrying is considered advantageous to avoid water contamination of the molecular sieve adsorbent. Predrying, however, is not mandatory.

The run was commenced using technical grade normal hexane purge containing no branched-chain polyolefin polymer. The technical grade normal hexane purge medium was not recycled and technical grade normal hexane purge containing no branched-chain polyolefin polymer was continuously used as the purge medium.

Table II sets forth typical process data for the adsorption step effluent stream, the copurge step effluent stream and the countercurrent purge step effluent stream exiting the 14 foot reactor column adsorber for representative cycle number 263.

TABLE II

| | DATA FROM CYCLE 263 | | |
|---|---|---|---|
| Stream | Wt % Polymer In Hexane | Weight Hexane (g) | Weight Polymer In Hexane (g) |
| Adsorption Effluent | 3.68 | 510.6 | 19.7 |
| Copurge Effluent | 2.88 | 307.8 | 8.9 |
| Desorption Effluent | 0.09 | 2,143.6 | 1.9 |

The data of Table II demonstrates that since no branched-chain polyolefin ($C_8$ polymer and greater, i.e., $C_{12}$, $C_{16}$ etc.) was present in the technical grade normal hexane fed into the adsorber as purge prior to and during cycle 263, the branched-chain polyolefin appearing in the adsorption step, copurge step, and countercurrent purge step effluent stream is polymer formed in the adsorber during the adsorption-desorption separation process.

The data of Table II show that the concentration of branched-chain polyolefin ($C_8$ and greater polymer) is about 32 and 43 times higher based on normal hexane present in the adsorption step and copurge step effluents respectively compared with the concentration of branched-chain polyolefin based on normal hexane in the countercurrent purge step effluent stream. Further, it can be seen that the combined normal hexanes from the adsorption step and copurge step effluent streams amount to about only 27.6 percent of the total normal hexane purge medium fed to the adsorber. However, the combined adsorption step and copurge step effluent streams contain about 93.8 weight percent of the branched-chain polyolefin formed in the adsorber. This is the first key discovery upon which the process in accordance with the preisent invention is predicated.

Subsequent to cycle 263, a technical grade normal hexane purge medium containing a nominal 0.45 weight percent branched-chain polyolefin (of the same type produced in the adsorber) based on normal hexane was used as copurge step and countercurrent purge step purge medium feed. The normal hexane purge medium was not recycled and the normal hexane purge medium containing a nominal 0.45 weight percent polymer was used continuously as purge medium feed.

Some typical representative process data for representative process cycles are set forth in Table III.

TABLE III

| Cycle Number | Wt % Polymer In Desorption Product Hexane | Wt % Polymer In Feed Hexane |
| --- | --- | --- |
| 309 | 0.46 | 0.43 |
| 320 | 0.46 | 0.44 |
| 335 | 0.46 | 0.45 |
| 351 | 0.43 | 0.45 |
| 369 | 0.44 | 0.46 |
| 381 | 0.43 | 0.44 |

Table III shows that the normal hexane purge medium fed as purge in the copurge and countercurrent purge step contained about 0.45 weight percent branched-chain polyolefin. Table III also demonstrates that the weight percent of branched-chain polyolefin based on hexane in the countercurrent purge step effluent stream is essentially the same as the weight percent of branched-chain polyolefin based on hexane present in the purge medium feed for the copurge and countercurrent purge steps at these polymer levels. This is the second key discovery upon which the process in accordance with the present invention is predicated.

Using this data, the surprising advantages of the process in accordance with the present invention may be conveniently demonstrated in comparison with the prior art as disclosed in U.S. Pat. No. 3,721,064 to Symoniak et al.

In accordance with the process of the present invention, the polymer containing normal hexane product recovered from the countercurrent purge step effluent by the normals product dehexanizer (such as fractional distillation column 51 of FIG. 1) is recycled directly as normal hexane purge medium without separation of the branched-chain polyolefin polymer ($C_8$ and greater polymer) from the straight chain normal hexane ($C_6$). Furthermore, in accordance with the process of the present invention, at least a portion of the polymer containing normal hexane product recovered from the combined adsorption step and copurge step effluent streams by the isomer products dehexanizer (such as fractional distillation column 71 of FIG. 1) is passed through a separation unit (such as polymer removal fractional distillation column 60) for separation of the branched-chain polyolefin ($C_8$ and greater polymer) from the normal hexane ($C_6$) to obtain a "clean" normal hexane for recycle as purge.

In contrast, the prior art combined and admixed the polymer containing normal hexane from the normals product dehexanizer and the isomer product dehexanizer and passed at least a portion of this admixed polymer containing hexane through a separation unit for separation of the branched-chain polyolefin from the normal hexane to obtain "clean" normal hexane for recycle as purge.

Figure 2:
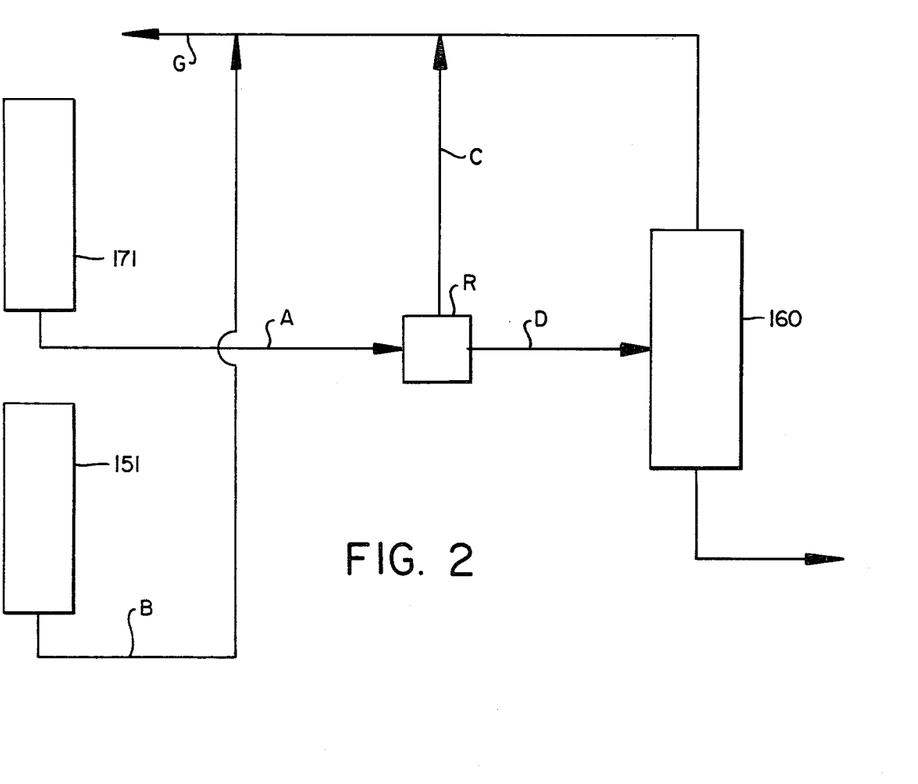
FIG. 2 is a flow diagram illustrating a preferred polymer removal scheme in accordance with the process of the present invention.
Figure 3:
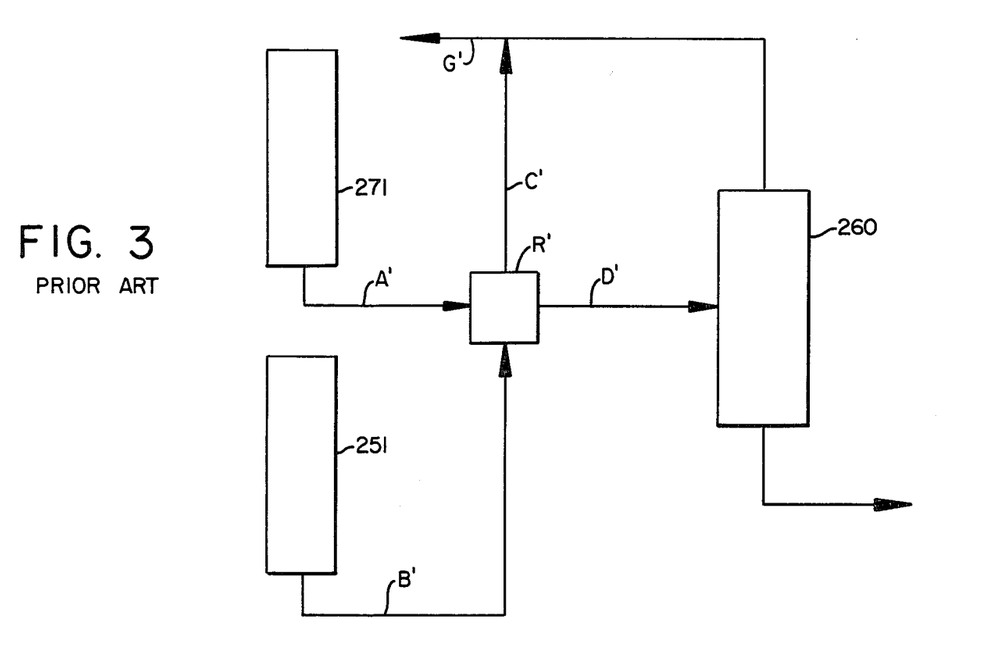
FIG. 3 is a schematic flow diagram illustrating a polymer removal scheme in accordance with the prior art practice.

FIG. 2 is a flow diagram illustrating a preferred polymer removal scheme in accordance with the process of the present invention. FIG. 3 is a flow diagram illustrating a polymer removal scheme in accordance with prior art practice.

Referring to FIG. 2, stream A is the isomer product dehexanizer separation unit 171 polymer containing hexane product effluent stream which passes to reservoir R. Stream B is the normals product dehexanizer separation unit 151 polymer containing hexane effluent stream which is recycled directly as purge medium via stream G in accordance with the process of the present invention.

Referring to FIG. 3, stream A' is the isomer product dehexanizer separation unit 271 polymer containing hexane product effluent stream which passes to reservoir R'. Stream B' is the normals product dehexanizer separation unit 251 polymer containing hexane effluent stream which passes to reservoir R' in accordance with prior art practice.

For purposes of simplifying the polymer material balance, the assumption is made that reservoirs R and R' and polymer separation units 160 and 260 accumulate no polymer. This simplification merely permits convenient comparison of both schemes but does not substantially affect the comparative results.

Branched-chain polyolefin ($C_8$ and greater polymers) appear in each of effluent streams A, A', B and B' from two sources. First, polymer is formed in the adsorbers and secondly, previously recycled polymer is recovered as hereinbefore discussed. The amount of hexane and polymer in streams A, A' are equivalent and streams B, B' are equivalent.

Let $X$ = the quantity of polymer recycled to the adsorbers in the purge medium hexanes.

Let $Y$ = the amount of polymer formed in the adsorbers.

From Table III data, it is shown that the weight percent of polymer based on hexane in the feed purge will be essentially equal to the weight percent based on hexane of recycled polymer present in countercurrent effluent stream passed to the normals product dehexanizer separation unit. From Table II, it is shown that 72.4 percent of normal hexane purge medium is present in the countercurrent purge effluent stream. From this, it is seen that 72.4 percent of the recycled polymer is present in effluent streams B and B' from the normals product dehexanizer separation units 151 and 251. Likewise, 27.6 percent of the recycled polymer is present in streams A and A' from the isomer product dehexanizer separation units 171 and 271.

From Table II, it is shown that 93.8 percent of the polymer formed in an adsorber will be in the combined adsorption step and copurge step effluent stream and thus 93.8 percent of the polymer formed in an adsorber is present in effluent streams A and A' from the isomer product dehexanizer separation units 171 and 271. Likewise, 6.2 percent of the polymer formed in the adsorbers is present in effluent streams B and B' from the normal products dehexanizer separation units 151 and 251.

Thus the polymer present in streams A and $A' = 0.276X + 0.938Y$.

The polymer present in streams B and $B' = 0.724X + 0.062Y$.

In the prior art scheme of FIG. 3, streams A' and B' are combined in reservoir R' resulting in a polymer quantity $(X+Y)$ which is the amount of polymer recycled in the purge medium hexanes plus polymer which is formed in the adsorbers. A fraction f' of this sum $(X+Y)$ is then fed by stream D' to polymer separation unit 260 leaving the polymer quantity $(1-f')(X+Y)$ to be recycled by stream C' with the hexane purge medium to stream G' for recycle to the adsorbers.

As an initial condition, it will be assumed that there is no polymer present in the purge medium normal hexane when the process cycles start. If f' is selected to be 0.276 and all of effluent stream A of FIG. 2 (present invention) is fed to polymer separation unit 160 by stream D, then the same fraction of polymer containing hexanes will be fed to polymer separation units 160 and 260 of the schemes of FIG. 2 (present invention) and FIG. 3 (prior art).

The results of the process in accordance with the present invention are tabulated in Table IV and the results of the prior art scheme are tabulated in Table V based on the foregoing conditions for a hypothetical 10 cycle run. One skilled in the art will appreciate that the data are representative of the results that may be expected to be achieved over a large number of cycles, e.g., 1000 or more cycles. Polymer formation amount Y is assumed to decrease from 9 to 0 over the 10 hypothetical cycles since it is known that polymer formation decreases with increasing numbers of cycles in accordance with the hereinbefore described process. Polymer removed (Z) by polymer separation unit 160 in accordance with the present invention is given by: $Z = 0.276X + 0.938Y$. Polymer removed (Z') by polymer separation unit 260 in accordance with the prior art practice is given by: $Z' = 0.276(X + Y)$. X in both cases is initially zero for purposes of this example. In both the cases of Table IV and Table V, 27.6 percent of the total polymer containing hexane from normals and isomer product dehexanizers is processed in polymer separation units 160 and 260 respectively.

TABLE IV
(Present Invention)

| Cycle Number | Polymer Recycled (X) | Polymer Formed (Y) | Polymer Removed In Stripper (Z) | Polymer Recycled To Next Step |
|---|---|---|---|---|
| 1 | 0.000 | 9 | 8.442 | 0.558 |
| 2 | 0.558 | 8 | 7.658 | 0.900 |
| 3 | 0.900 | 7 | 6.814 | 1.086 |
| 4 | 1.086 | 6 | 5.928 | 1.158 |
| 5 | 1.158 | 5 | 5.010 | 1.148 |
| 6 | 1.148 | 4 | 4.069 | 1.079 |
| 7 | 1.079 | 3 | 3.112 | 0.967 |
| 8 | 0.967 | 2 | 2.143 | 0.824 |
| 9 | 0.824 | 1 | 1.165 | 0.659 |
| 10 | 0.659 | 0 | 0.182 | 0.477 |
| TOTALS | | 45 | 44.523 | |

TABLE V
(Prior Art)

| Cycle Number | Polymer Recycled (X) | Polymer Formed (Y) | Polymer Removed In Stripper (Z') | Polymer Recycled To Next Step |
|---|---|---|---|---|
| 1 | 0.000 | 9 | 2.484 | 6.516 |
| 2 | 6.516 | 8 | 4.006 | 10.510 |
| 3 | 10.510 | 7 | 4.883 | 12.677 |
| 4 | 12.677 | 6 | 5.155 | 13.522 |
| 5 | 13.522 | 5 | 5.112 | 13.410 |
| 6 | 13.410 | 4 | 4.805 | 12.605 |
| 7 | 12.605 | 3 | 4.307 | 11.298 |
| 8 | 11.298 | 2 | 3.670 | 9.628 |
| 9 | 9.628 | 1 | 2.993 | 7.695 |
| 10 | 7.695 | 0 | 2.124 | 5.571 |
| TOTALS | | 45 | 39.429 | |

The data of Table IV (present invention) shows that 45 units of polymer are formed in the adsorbers during the 10 cycles and 44.523 units of polymer are removed by polymer separation unit or stripper 160 in accordance with the process of the present invention for the conditions stated. In comparison the data of Table V (prior art) shows that 45 units of polymer are formed in the adsorbers during the 10 cycles and only 39.429 units of polymer are removed by polymer separation unit or stripper 260 in accordance with the prior art practice.

A further comparison of the data of Tables IV and V shows that in the process in accordance with the present invention the amount of polymer available for recycle to the adsorbers after each cycle is surprisingly 11.7 times less than the amount of polymer available for recycle to the adsorbers in accordance with the prior art practice. This significantly reduces the chances of producing higher molecular weight polymers from a recycled polymer. This is of importance in that it reduces the possibility of fouling the adsorbent bed which condition would be aggravated by higher molecular weight polymers formed on recycle of polymer and would likely increase the on-stream time of the adsorber beds before regeneration was required.

It should again be noted that in the Table IV and Table V schemes, the same amount of polymer containing hexane was processed by the polymer separation unit or stripper. Thus, the process in accordance with the present invention will achieve significantly improved results (11.7 times less power recycled when the purge medium initially contains zero polymer) from polymer removal processing using the same size polymer separation unit as in the prior art scheme.

The process in accordance with the present invention will now be compared with the prior art scheme for the case of Table V wherein the process in accordance with the present invention will recycle approximately the same amount of polymer per cycle to the adsorbers as the prior art scheme of Table V.

This can be accomplished if 60 percent of the polymer containing hexane of stream A (FIG. 2) is passed to polymer separation unit or stripper 160 by stream D. Thus, 40 percent of the polymer containing hexane of stream A is recycled via stream C directly as purge mediun to the adsorbers by stream G.

In this instance only about 16.6 percent of the polymer containing hexane is processed in accordance with the process of the present invention. Polymer removed (Z) by the polymer separation unit or stripper 160 is given by the equation $0.6 \ (0.276X + 0.938Y)$. Initial conditions are the same as for Tables IV and V. Results are set forth in Table VI.

TABLE VI
(Present Invention)

| Cycle Number | Polymer Recycled (X) | Polymer Formed (Y) | Polymer Removed In Stripper (Z) | Polymer Recycled To Next Step |
|---|---|---|---|---|
| 1 | 0.000 | 9 | 5.065 | 3.935 |
| 2 | 3.935 | 8 | 5.154 | 6.781 |
| 3 | 6.781 | 7 | 5.063 | 8.718 |
| 4 | 8.718 | 6 | 4.821 | 9.897 |
| 5 | 9.897 | 5 | 4.453 | 10.444 |
| 6 | 10.444 | 4 | 3.981 | 10.463 |
| 7 | 10.463 | 3 | 3.421 | 10.042 |
| 8 | 10.042 | 2 | 2.789 | 9.253 |
| 9 | 9.253 | 1 | 2.095 | 8.158 |
| 10 | 8.158 | 0 | 1.351 | 6.807 |
| Totals | | 45 | 38.193 | |

Comparing the results of Table VI (present invention) with the results of Table V (Prior Art), it is seen that the process in accordance with the present invention will recycle approximately the same amount (generally lower) of polymer to the adsorbers and will remove approximately the same amount of polymer from the hexane (within 3 percent) when the process in accordance with the present invention processes only 16.6 percent of the polymer containing hexane in a polymer separation unit compared to the prior art case processing 27.6 percent of the polymer containing hexane in a polymer separation unit. Thus, the process in accordance with the present invention achieves essentially the same polymer removal results as the prior art when processing about 40 percent less polymer containing hexane than the prior art.

The process in accordance with the present invention will therefore achieve essentially the same results as a prior art scheme with a significant reduction in the size and cost of the polymer separation unit required and a significant reduction in utilities requirements and costs. Estimates of some of the savings for the process in accordance with the present invention are set forth in Table VII.

TABLE VII

| Percent Reduction in Size or Cost Using Standard Estimating Techniques Compared with Prior Art | |
|---|---|
| Hexane Feed to $C_6/C_8$ + Stripper | −40 |
| $C_6/C_8$ + Stripper Column Diameter | −23 |
| $C_6/C_8$ + Stripper Cost | −14 |
| Reboiler Heat Transfer Area | −40 |
| Reboiler Steam Requirement | −40 |
| Reboiler Cost | −26 |
| Condenser Heat Transfer Area | −40 |
| Condenser Cooling Water Requirement | −40 |
| Condenser Cost | −26 |

The foregoing examples are based on the stated conditions. These examples are representative, however, of the results that may be achieved by the process in accordance with the present invention in comparison to the prior art over a wide range of actual operating conditions.

Although preferred embodiments of the present invention have been described in detail, it is contemplated that modifications may be made and that some features may be employed without others, all within the spirit and scope of the invention.

What is claimed is:

1. In a process for the separation of hydrocarbons in a vapor feed stream containing straight-chain and branched-chain monoolefin having from four to six carbon atoms inclusive comprising:

as an adsorption step,
passing said vapor feed stream into one end of an adsorber containing molecular sieve having a pore diameter of about 5 Angstroms and having adsorbed thereon a straight-chain paraffin hydrocarbon; and
obtaining from the other end of said adsorber a first effluent fluid stream exiting in vapor phase comprising branched-chain monoolefin, branched-chain polyolefin, and straight-chain paraffin hydrocarbon;

as a copurge step,
passing a first vapor purge stream containing straight-chain paraffin hydrocarbon into said one end of said adsorber; and
obtaining from said other end of said adsorber a second effluent fluid stream exiting in vapor phase comprising branched-chain monoolefin, branched-chain polyolefin, and straight-chain paraffin hydrocarbon;

as a countercurrent purge step,
passing a second vapor purge stream containing a straight-chain paraffin hydrocarbon into said other end of said adsorber; and
obtaining from said one end of said adsorber a third effluent fluid stream exiting in vapor phase comprising straight-chain monoolefin, branched-chain polyolefin, and straight-chain paraffin hydrocarbon;

wherein the partial pressure of the straight-chain paraffin hydrocarbon content of said first and second vapor purge streams is greater than the partial pressure of the straight-chain monoolefin content of the vapor feed stream and wherein said molecular sieve is partially loaded with straight-chain paraffin hydrocarbon during all of said adsorption, copurge and countercurrent purge steps; and separating said branched-chain monoolefin from said branched-chain polyolefin and said straight-chain paraffin hydrocarbon in said first and second effluent fluid streams, said separation providing a fourth effluent fluid stream comprising branched-chain polyolefin and straight-chain paraffin hydrocarbon;

separating said said straight-chain monoolefin from said branched-chain polyolefin and said straight-chain paraffin hydrocarbon in said third effluent fluid stream, said separation providing a fifth effluent fluid stream comprising branched-chain polyolefin and straight-chain paraffin hydrocarbon;

the improvement in which comprises:

(a) recycling said fifth effluent fluid stream comprising branched-chain polyolefin and straight-chain paraffin hydrocarbon for use in said first and second purge streams without separation of said branched-chain polyolefin from said straight-chain paraffin hydrocarbon in said fifth effluent fluid stream;

(b) introducing at least a portion of said fourth effluent fluid stream into a separation unit for separating said branched-chain polyolefin from said straight-chain paraffin hydrocarbon and obtaining from said separation unit a sixth effluent fluid stream comprising straight-chain paraffin hydrocarbon and a seventh effluent fluid stream comprising branched-chain polyolefin; and (c) recycling said sixth effluent fluid stream comprising straight-chain paraffin hydrocarbon for use in said first and second purge streams.

2. A process as recited in claim 1 wherein substantially all of said fourth effluent fluid stream is introduced into said separation unit.

3. A process as recited in claim 1 wherein the remaining portion of said fourth effluent fluid stream is recycled for use in said first and second purge streams without separation of said branched-chain polyolefin from said straight-chain paraffin hydrocarbon.

4. A process as recited in claim 1 wherein about 25 percent to 100 percent of said fourth effluent fluid stream is introduced into said separation unit.

5. A process as recited in claims 1, 2, 3 or 4 wherein said separation unit is a fractional distillation unit with said sixth effluent fluid stream comprising straight-chain paraffin hydrocarbon being recovered as overhead and said seventh effluent fluid stream comprising branched-chain polyolefin being recovered as bottoms.

6. A process as recited in claims 1, 2, 3 or 4 wherein said straight-chain paraffin hydrocarbon is normal hexane.

7. A process as recited in claims 1, 2, 3 or 4 wherein said straight-chain monoolefin is normal butenes and said branched monoolefin is isobutylene.

* * * * *

UNITED STATES PATENT AND TRADEMARK OFFICE
CERTIFICATE OF CORRECTION

PATENT NO. : 4,362,537  
DATED : December 7, 1982  
INVENTOR(S) : R. G. Werner

It is certified that error appears in the above-identified patent and that said Letters Patent are hereby corrected as shown below:

At Column 2, line 24 delete "absorber" and substitute -- adsorber -- therefor; line 28 delete "absorption" and substitute --adsorption-- therefor.

At Column 5, line 39 delete "absorber" and substitute --adsorber-- therefor; line 64 delete "between" and substitute --thereon-- therefor.

At Column 7, line 14 delete "absorber" and substitute --adsorber--; line 15 delete the words "absorber" and "absorbers" and substitute therefor the words --adsorber-- and --adsorbers-- respectively; line 17 delete "Absorber" and substitute --Adsorber-- therefor; line 19 delete "absorber" and substitute --adsorber-- therefor; line 21 delete "gase" and substitute --gas-- therefor; line 22 delete "absorber" and substitute --adsorber-- therefor; line 23 delete "absorption" and substitute --adsorption-- therefor; line 25 delete the words "absorption-desorption" and substitute the words --adsorption-desorption-- therefor.

At Column 8, line 21 delete "of" and substitute --for--.

At Column 10, line 5 delete "isomer-" and substitute --isomer-- therefor.

At Column 11, line 4 delete the words "adsorption-desportion" and substitute the words --absorption-desorption-- therefor; line 5 delete the word "so" at the end of the line and substitute the word --no-- therefor.

At Column 12, line 57 delete "preisent" and substitute --present-- therefor.

UNITED STATES PATENT AND TRADEMARK OFFICE
CERTIFICATE OF CORRECTION

PATENT NO. : 4,362,537

DATED : December 7, 1982

INVENTOR(S) : R. G. Werner

It is certified that error appears in the above-identified patent and that said Letters Patent are hereby corrected as shown below:

At Column 16, line 18 delete "power" and substitute --polymer-- therefor; line 33 delete "mediun" and substitute --medium-- therefor.

At Column 18, line 18 delete the word "said" following the word "separating".

Signed and Sealed this

Second Day of August 1983

[SEAL]

Attest:

Attesting Officer

GERALD J. MOSSINGHOFF

Commissioner of Patents and Trademarks